(12) United States Patent
McKay

(10) Patent No.: US 8,449,622 B2
(45) Date of Patent: May 28, 2013

(54) MULTI-PHASE OSTEOCHONDRAL IMPLANTABLE DEVICE

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1333 days.

(21) Appl. No.: 11/518,680

(22) Filed: Sep. 11, 2006

(65) Prior Publication Data
US 2008/0065210 A1  Mar. 13, 2008

(51) Int. Cl.
*A61F 2/28* (2006.01)

(52) U.S. Cl.
USPC ..................... 623/23.56; 623/23.57

(58) Field of Classification Search
USPC ............................. 623/23.56–23.58
See application file for complete search history.

(56) References Cited

U.S. PATENT DOCUMENTS

| | | | |
|---|---|---|---|
| 4,863,475 A * | 9/1989 | Andersen et al. | 128/898 |
| 5,290,494 A | 3/1994 | Coombes et al. | |
| 5,935,594 A * | 8/1999 | Ringeisen et al. | 424/426 |
| 6,017,366 A * | 1/2000 | Berman | 623/21.11 |
| 6,316,091 B1 | 11/2001 | Richart et al. | |
| 6,514,286 B1 | 2/2003 | Leatherbury et al. | |
| 6,586,388 B2 | 7/2003 | Oppermann et al. | |
| 2001/0038848 A1 | 11/2001 | Donda et al. | |
| 2003/0003127 A1 | 1/2003 | Brown et al. | |
| 2004/0230303 A1 * | 11/2004 | Gomes et al. | 623/16.11 |
| 2005/0031666 A1 | 2/2005 | Trieu | |
| 2006/0060209 A1 | 3/2006 | Shepard | |

FOREIGN PATENT DOCUMENTS
WO   WO98/38949   9/1998

OTHER PUBLICATIONS

Sawynok, Jana, Topical and Peripherally Acting Analgesics; Pharmacological Reviews, 2003; vol. 55, No. 1, pp. 1-20.

* cited by examiner

*Primary Examiner* — Thomas J Sweet
*Assistant Examiner* — Christopher D Prone
(74) *Attorney, Agent, or Firm* — Sorell Lenna & Schmidt LLP

(57) ABSTRACT

An osteochondral implantable device is provided, comprising an upper cap and at least one insert comprising a non-polymeric material in physical contact with the upper cap, said lower insert comprising at least one non-polymeric material, wherein the porosity of the upper cap is greater than the porosity of the insert and the Young's modulus of the upper cap is smaller than the Young's modulus of the insert.

34 Claims, 4 Drawing Sheets

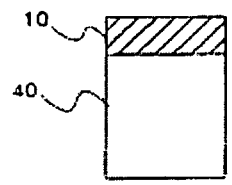
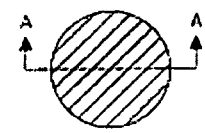
Fig. 1　　　　　　　　Fig. 2
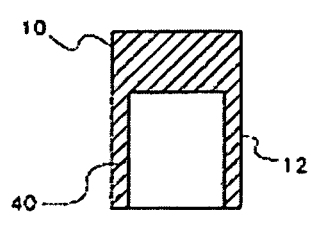
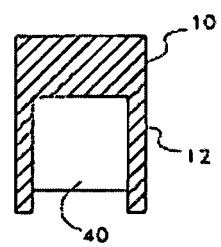
Fig. 2A　　　　　　　Fig. 2B
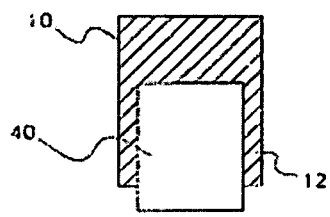
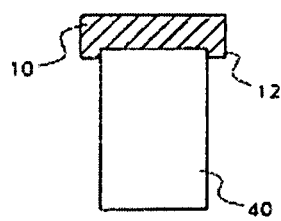
Fig. 2C　　　　　　　Fig. 2D

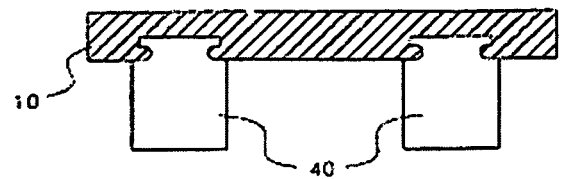
Fig. 5
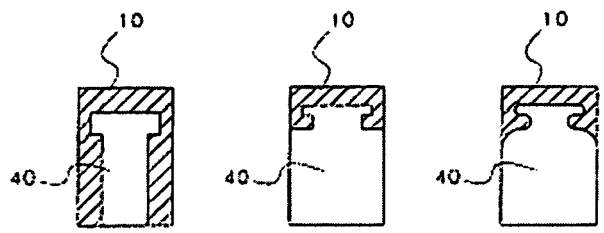
Fig. 6A     Fig. 6B     Fig. 6C
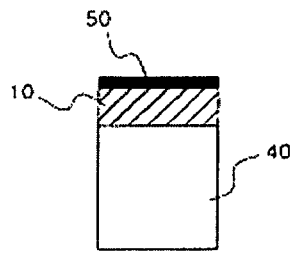     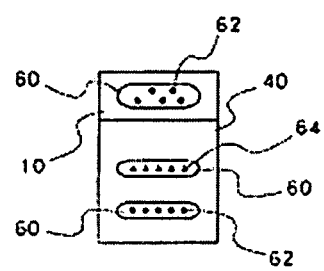
Fig. 7     Fig. 8

MULTI-PHASE OSTEOCHONDRAL IMPLANTABLE DEVICE

FIELD OF THE INVENTION

The present invention relates generally to osteochondral implantable devices.

BACKGROUND

The use of prosthetic devices for treatment of bone injuries/illnesses is continuously expanding with an increasingly active and aging population. Among those disorders are osteoporosis, Paget's disease of bone and joints, and arthritis. All these disorders may cause limited mobility and often, particularly in the elderly, can result in death due to resulting bone fractures. When not fatal, these disorders still often require surgical bone or joint replacement of hips, knees, elbows, and other joints.

The major problem associated with the bone replacement, especially for the defects of both the bone and the adjacent cartilage, is the lack of a suitable material which would have the same or similar properties as bone but that would also be compatible with the human body. The properties which the bone or joint replacement material need to possess include biocompatibility, porosity, strength, durability, elasticity and, in order to prevent wear in joint areas and to prevent or allow tissue attachment in other areas, as need be, a possibility to be surface finished. Therefore, such material must have approximately the same porosity, weight and structure and must not be more fragile or more brittle than the normal bone.

Current research is focused around the use of porous degradable synthetic polymer materials as osteochondral plug scaffolds to allow regeneration of both the subchondral bone and hylan cartilage surface. Some have even added in small amounts of calcium phosphate or calcium sulfate directly blended into the polymer scaffold to facilitate bone formation. Animal studies show that the underlying subchondral bone results in either large unresorbed areas of polymer or void spaces filled with fluid or fibrous tissue. This void space in the subchondral bone can often result in a collapse of the upper cartilage surface and suboptimal repair of the hylan cartilage layer with the host hylan cartilage. Thus, the "one size fits all" approach hinders implant incorporation into the host bone and cartilage and eventual replacement by natural host tissue.

Accordingly, there is a need for improved osteochondral implantable devices suitable for repair of bone/cartilage defects.

SUMMARY OF INVENTION

The instant invention overcomes these and other drawbacks of the prior art by providing novel osteochondral implantable device comprising: an upper cap; and at least one insert in contact with the upper cap, said at least one insert comprising at least one non-polymeric material; wherein a porosity of the upper cap is greater than a porosity of the at least one insert, and a Young's modulus of the upper cap is smaller than a Young's modulus of the at least one insert.

In different embodiments of the invention, the upper cap comprises a polymer, such as natural or biodegradable synthetic or non-biodegradable synthetic polymer or a combination thereof. The at least one insert comprises a non-polymeric material such as, for example, a ceramic, a bone or a combination thereof. The upper cap may further comprise a portion forming a collar portion, which serves to secure the at least one insert. In another embodiment, the invention provides a bone void filler comprising the osteochondral implantable device.

In another aspect, the invention further comprises at least one bioactive agent which is included into at least one of the upper cap or the at least one insert. In different embodiments of the invention, the at least one bioactive agent comprises cells, growth factors, pain-reducing agents, anti-inflammatory agents, antibiotics, and any combination thereof.

In yet another aspect, the invention provides a kit comprising an upper cap; and at least one insert, said the at least one insert comprising at least one non-polymeric material; wherein a porosity of the upper cap is greater than a porosity of the at least one insert, and a Young's modulus of the upper cap is smaller than a Young's modulus of the at least one insert. In different embodiments, the kit may further comprise a set of instructions, at least one bioactive agent, a bioadhesive, or any combination thereof. In the assembled form, these parts of the kit form an osteochondral implantable device or a bone void filler.

BRIEF DESCRIPTION OF THE DRAWINGS

FIG. 1 shows an embodiment of the osteochondral implantable device wherein the upper cap does not include a collar portion.

FIGS. 2A-D show different embodiment of the osteochondral implantable device where the upper cap includes differently shaped collar portions.

FIG. 5 shows an embodiment wherein the implantable device of the instant invention comprises more than one insert.

FIGS. 6A-C shows an embodiment of the osteochondral implantable device where the upper cap is molded around the at least one insert.

FIG. 7 shows an embodiment of the osteochondral implantable device further comprising a polymeric film.

FIG. 8 shows an embodiment of the osteochondral implantable device wherein both the upper cap and the at least one insert comprise reservoirs filled with a bioactive agent.

DESCRIPTION OF THE PREFERRED EMBODIMENTS

Novel concept of the instant invention involves the design of osteochondral implantable devices with two separate materials fixed together so that the optimal material can be utilized to repair the subchondral bone and cartilage surface.

In one aspect, the osteochondral implantable device of the instant invention comprises two parts: an upper cap 10 and the at least one insert 40 (FIG. 1) which are fixed together. A person of ordinary skill in the art would appreciate that the upper cap and the at least one insert may assume various shapes to better serve the needs of the patient. For example, in an embodiment shown in FIG. 1, the upper cap 10 is on top of the at least one insert 40 and does not cover any other surfaces of the at least one insert. The upper cap 10 and the at least one insert may be fixed together by multiple means, including, without limitations, a bioadhesive. Preferably, the bioadhesive is biodegradable, with the rate of degradation sufficient to allow bone and cartilage ingrowth into the at least one insert and the upper cap, respectively.

A person of the ordinary skill in the art will appreciate that the practitioner may adjust the size and the shape of the tissue defect to about the size of the at least one insert. Thus, the device of the present invention will be held tight in the tissue defect without a need for a fixation device which is embedded within the osteochondral implantable device and insertable into a tissue receptacle.

In other embodiments, representative examples of which are shown in FIG. 2, the upper cap additionally comprises a collar portion 12 (FIGS. 2A-D). The collar portion 12 forms a receptacle which accepts at least a portion of the at least one insert 40. A person of ordinary skill in the art will understand that "at least the portion" of the at least one insert includes the whole length of the at least one insert. In different embodiments of the invention, the collar portion 12 may comprise a single structure.

Figure 3A:
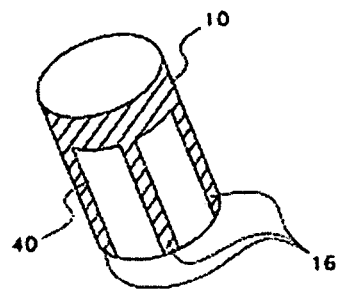
FIGS. 3A-D show yet different embodiments of the osteochondral implantable device where the collar portion has extensions protruding in axial direction only (FIG. 3A) or in both axial and circumferential directions (FIGS. 3B-3D).
Figures 3B, 3C:
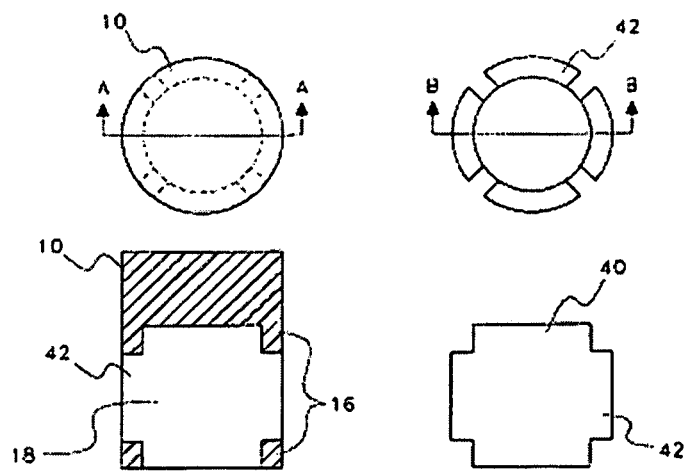
Figure 3D:
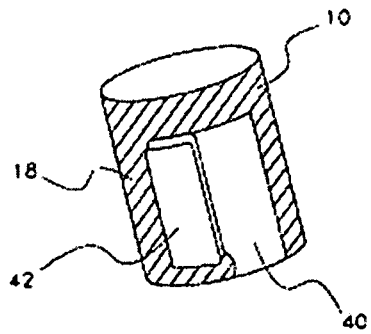

In another embodiment, the collar portion may be comprised of a plurality of extensions 16 (FIG. 3A). The shape of the extensions 16 may also differ. For example, these extensions may be in axial direction only or both in axial and circumferential directions (FIGS. 3B-D). The latter embodiment is especially suitable if the at least one insert 40 is shaped with protrusions 42 which would provide an additional level of securing the at least one insert 40 in the collar portion 12 of the upper cap 10. One example of such securing is via a bayonet-type connection. Alternatively, a groove or grooves on the internal surfaces of the collar portion 12 may be used in combination with protrusion or protrusions of the at least one insert 40 to form a threaded connection. Alternatively, the collar portion of the upper cap may comprise protrusions extending the radial direction, which accept grooves 44 of the at least one upper cap.

A person of the ordinary skill in the art will undoubtedly understand that the at least one insert may be secured to the upper cap by a combination of the bioadhesive and mechanical means, such as, for example, by using matching and locking shapes of the upper cap and the ceramic insert, including the shapes described above.

Figure 4A:
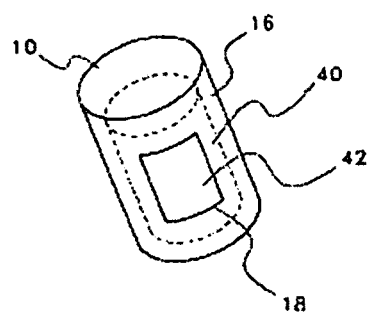
FIGS. 4A-E show yet another embodiment wherein the collar portion of the upper cap comprises one or more windows.
Figure 4B:
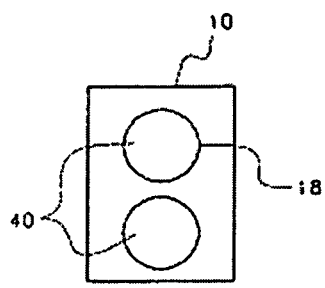
Figure 4C:
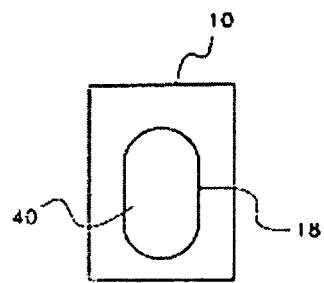
Figure 4D:
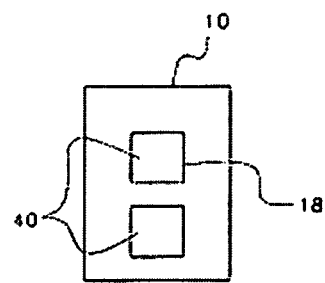
Figure 4E:
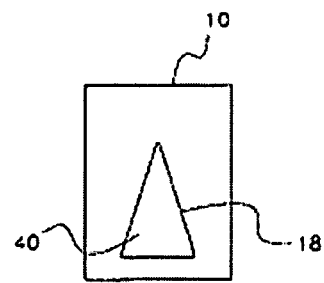

In another embodiment, the collar portion 12 may further comprise a window 18 (FIG. 4A). In different embodiments of the invention, the window 18 may assume different shapes, such as rectangle, oval, triangle, etc. Suitable non-limiting examples of the window shapes are shown in FIGS. 4B-E.

A person of ordinary skill would also appreciate that the collar portion 12 may have receptacles for more than one insert 40. An embodiment of the instant invention shown in FIG. 5 shows the upper cap 10 wherein the collar portion 12 forms two receptacles for two inserts 12.

Preferably, the mechanical properties of the upper cap and the at least one insert approximately match the properties of the tissues which are intended to be grown into those structures. For example, in one embodiment, the upper cap is intended to be in contact with cartilage while the at least one insert is intended to be in contact with bone. In such embodiment, it would be advantageous to form the at least one insert of a material or materials which approximately match mechanical properties of the bone. By the same token, it would be beneficial to form the upper cap of a material or materials which approximately match the properties of cartilage. In such embodiment, the at least one insert will have a higher Young's modulus and a lower porosity than the upper cap.

For example, the upper cap may be formed of polymers, such as synthetic biodegradable polymers, synthetic non-biodegradable polymers, natural polymers, or any combination thereof. The suitable non-limiting examples of synthetic biodegradable polymers include α-hydroxy acids, such as poly-lactic acid, polyglycolic acid, enantioners thereof, co-polymers thereof, polyorthoesters, and combinations thereof.

The suitable non-limiting examples of synthetic non-biodegradable polymers include hydrogels such as PVA, delrin, polyurethane, polyethylene, co-polymers thereof and any combinations thereof.

The natural polymers suitable for the upper cap include, without limitations, collagen, elastin, silk, hyaluronic acid, chytosan, and any combinations thereof.

Since at least some of these polymers are generally hydrophobic, it may be advantageous to add compounds which increase the hydrophilic properties of these polymers and thus promote entrance of intercellular fluids into the pores of those polymers. Suitable compounds include, without limitation, surfactants. Preferably, the surfactants are physiological surfactants, including, without limitation, non-toxic anionic, cationic, amphoteric or nonionic surfactant compatible with a bioactive agent and the materials of the upper cap and/or the at least one insert. Specific examples of such surfactants include, without limitation, metal soaps of fatty acids, alkyl aryl sulfonic acids, linear aklylbenzene sulfonates, alky sulfates, alcohol ethoxylates, alcohol ethoxy sulfates, alkylphenol ethoxylates, alpha olefin sulfonates, secondary alkane sulfonates, and alpha olefin sulfonates, as disclosed in U.S. Pat. No. 5,935,594 (Ringeisen), incorporated herein by reference in its entirety.

In one embodiment, the upper cap is made of a polymer of an α-hydroxy acid. Polymers comprising different α-hydroxy acids (such as PLA and PGA) in different ratios have different degradation times. A number of factors affect the degradation rate of PLA:PGA copolymers, such as molecular weight, copolymer ratio, polymer crystallinity, thermal history, shape and porosity, and wettability. Additionally, other factors such anatomical site of implant, vascularity, tissue interaction and patient response affect the degradation rate in vivo. Depending on the above listed factors, degradation rates for PLA and PGA polymers have been reported as low as 7 days for 50:50 PLG to several years for PLA. The overall degradation kinetics have been fairly well established for the entire family of homopolymers and copolymers. The experiments revealing relationship between the composition of the polymer and its degradation time are discussed in more details, for example, in U.S. Pat. No. 6,514,286 (Leatherbury) incorporated herein by reference in its entirety. Thus, varying relative contents of PLA and PGA, a person of the ordinary skill in the art would be able to create the upper cap with a pre-determined degradation time.

The methods of producing solid polymers are described, for example, in U.S. Pat. No. 5,290,494 (Coombes) incorporated herein by reference in its entirety. Generally, these methods involve the steps of: (1) polymer dissolution in a solvent; (2) casting the solution in a mold; (3) gel formation in situ; (4) removal of the shaped gel from the mold; and (5) drying to obtain solid material in relatively thick sections.

A person of the ordinary skill in the art would recognize that the upper caps of the desired shape may be pre-made by molding the polymeric mass in the molds of the desired shape. For example, the polymer may be molded around at least a portion of the at least one insert, preferably, if the portion of the at least one ceramic insert which is in contact with the polymer comprises a shape change, such as, for example, a groove or a protrusion. Thus, when the polymer is molded, the upper cap and the at least one insert are fixed together (FIGS. 6A-C). Alternatively, the upper caps of the desired shape may be cut from the polymeric mass after molding.

If the upper cap comprises polyorthoesters, a person of ordinary skill in the art will appreciate that several approaches can be useful for manufacturing a porous upper cap comprising polyorthoesters. For example, in one embodiment, it may be possible to mix polyorthoesters and a porogen (e.g., sodium chloride). Such mixture can be cured and then the porogen may be dissolved resulting in an open cell foam in which the pore size corresponds to the size of the porogen particles.

In another embodiment, saturating the POE with carbon dioxide under pressure and then releasing the pressure may be used. This method is similar to a method used to foam polystyrene and polypropylene. In yet another embodiment, one may also use a blowing agent that creates a foam as the POE cures.

In another embodiment, one may choose to electrospin a polyorthoester to form a nonwoven scaffold. This is an approach that is being widely investigated in the tissue engineering field.

A person of the ordinary skill in the art will also appreciate that multiple sources exist, which are suitable for the at least one insert. In one embodiment, the at least one insert may be formed from ceramic materials. These materials preferably include porous calcium phosphate, such as, for example, hydroxyapatite (HA), tri-calcium phosphate (TCP) calcium phosphate dibasic, calcium sulfate, calcium carbonate, or any combination thereof. In one set of embodiments, the content of HA varies between about 12% and about 50%, including, without limitations, a ceramic comprising approximately 30% HA and approximately 70% TCP, and a ceramic comprising approximately 15% HA and 85% TCP.

Several processes have been developed for synthesizing bioceramic parts incorporating more or less controlled macroporous architecture. Macroporous ceramics are generally obtained by adding porogenic agents, such as naphtalene or camphor particles, polymer microbeads of polyethylene, polymethyl metacrylate, PVB and the like, during the shaping step of the ceramic part by slip casting or dry pressing. The porogenic particles are sublimated or thermally decomposed before the final thermal densification treatment, thus leaving their mark in the form of pores in the final ceramic product. Other techniques, such as those reported in the European patent application EP-A-253506 or in the international patent application WO 98/38949 are also applicable. Another possible way for obtaining calcium phosphate bodies with interconnected macroporosity is to exchange the carbonate ions of a coral block against orthophosphate ions in aqueous solutions of phosphates under high temperature and pressure; the so obtained ceramic parts have the crystallographic structure of HA and the porous structure of the parent coral. Yet another suitable non-limiting example of preparation of the at least one insert is described in U.S. Pat. No. 6,316,091 (Richart), incorporated herein by reference in its entirety. Briefly, that process involves melting together PMMA beads of a desired ultimate ceramic pores size and pouring the calcium phosphate slurry into the PMMA beads melted together. After that, PMMA is burned out and the resulting composition is cintered to high temperatures to convert the calcium phosphate to the desired HA/TCP ratio.

A person of the ordinary skill in the art would undoubtedly understand that these methods of manufacturing the at least one insert are not exclusive: other methods also exist in the art. The instant invention is not limited only to inserts produced the methods recited above and includes the inserts manufactured by other methods.

In yet another embodiment, the at least one insert may be comprised of a bone, or a combination of the bone and the ceramic. The bone may be derived from an autologous source (the patient himself), or the allogeneic source (such as, for example, the patient's relatives or fresh cadavers) or a xenographic source (a donor of a different species, preferably, of a close species, such as a primate, if the patient is human). In one specific embodiment, the bone is derived from an allogeneic source, i.e., is an allograft bone.

The allograft bone is readily available from cadavers and avoids the surgical complications and patient morbidity associated with harvesting autologous bone. Human allograft tissue is widely used in orthopaedic surgery. Allograft tissue is strong, integrates with the recipient host bone, and can be shaped either by the surgeon to fit the specific defect or shaped commercially by a manufacturing process. Allograft bone is available in two basic forms: cancellous and cortical. Cortical bone is a highly dense structure comprised of triple helix strands of collagen fiber reinforced with hydroxyapatite. The hydroxyapatite component is responsible for the high compressive strength and stiffness of bone while the collagen fiber component contributes to its elastic nature, as well as torsional, shear, and tensile strength. Cortical bone is the main load-bearing component of long bones in the human body.

Many devices of varying shapes and forms can be manufactured from cortical allograft tissue. Surgical implants such as pins, rods, screws, anchors, plates, and intervertebral spacers have all been made and used successfully in human surgery.

It is further envisioned that in yet another embodiment, the bone may be modified for an improved attachment of growth factors, such as, for example, BMP, or for improved ingrowth of the host bone cells into the implantable device. For example, in one embodiment, the bone surface may be modified by oxygen plasma treatment, as described, for example, in U.S. application Ser. No. 11/339,781 (McKay et al., filed on Jan. 25, 2006).

In yet another embodiment of the invention, the at least one insert may be formed by a combination of a bone and a ceramic. These components may be joined together by a bioadhesive or by a changes in their geometry which hold the ceramic and the bone together (such as, for example, grooves and corresponding protrusions). One example of a suitable geometry change connection allowing attachment of the ceramic component to the bone component is a threaded connection. For example, in one embodiment, one component of the at least one insert (e.g., the ceramic) may have an opening into which the bone component is threadably attached. Other methods of joining these two components will be apparent to a person of the ordinary skill in the art without departing from the letter and the spirit of the instant invention.

A person of the ordinary skill would further appreciate that the ceramic or the bone, or the combination thereof may damage adjacent articulating cartilage surfaces, so polymers are better suited for cartilage repair. Polymers are more soft and compliant for the cap of the osteochondral plug. Their degradation products also cause less tissue reaction than when encased in subchondral bone, so they are more appropriate at this location. All these improvements to the current state of the art in cartilage repair will facilitate the plugs incorporation and eventual replacement by natural host tissue and incorporated into the adjacent host tissue.

In another embodiment, the osteochondral implantable device further comprises a film 50 above the upper cap 10 to prevent synovial fluid from entering the osteochondral implantable device (FIG. 7). Preferably, the film 50 is formed of a non-porous polymeric material. Suitable materials include, without limitation polymers, such as synthetic biodegradable polymers, synthetic non-biodegradable polymers, natural polymers, or any combination thereof. Briefly, the materials suitable for the upper cap 10 and described above are also suitable for the film 50. Preferably, the film 50 is composed of a biodegradable polymer. A person of ordinary skill in the art will recognize that the biodegradable polymer used for the film 50 should preferably not be porous or water permeable. Thus, during preparation of the film 50, it is not necessary to add porogens, as described above.

A person of the ordinary skill in the art would appreciate that the osteochondral implantable device of the instant invention also allows for optimal loading of its porous structure with bioactive agents, such as, for example, growth factors or cells. The calcium phosphate insert inherently binds osteogenic bone growth factors to facilitate bone formation that synthetic polymers can not. It also has sufficient residence time in the patient to allow new bone to form before it is degraded by the body that synthetic polymers often don't. The bioactive agent may be included within the upper cap, or within the at least one insert or within both the upper cap and the at least one insert. Suitable bioactive agents include, without limitation, growth factors (including osteogenic and chondrogenic agents), anti-inflammatory agents, pain-reducing agents, antibiotics, cells, and any combinations thereof.

Growth factors suitable for use in the practice of the invention include but are not limited to bone morphogenic proteins, for example, BMP-2, rhBMP-2, BMP-4, rhBMP-4, BMP-6, rhBMP-6, BMP-7[OP-1], rhBMP-7, GDF-5, and rhGDF-5, as disclosed, for example, in the U.S. Pat. Nos. 4,877,864; 5,013,649; 5,661,007; 5,688,678; 6,177,406; 6,432,919; 6,534,268, and 6,858,431, and in Wozney, J. M., et al. (1988) *Science,* 242(4885):1528-1534. Growth factors suitable for use in the practice of the invention include but are not limited to bone morphogenic proteins, for example, BMP-2, rhBMP-2, BMP-4, rhBMP-4, BMP-6, rhBMP-6, BMP-7[OP-1], rhBMP-7, GDF-5, and rhGDF-5, as disclosed, for example, in the U.S. Pat. Nos. 4,877,864; 5,013,649; 5,661,007; 5,688,678; 6,177,406; 6,432,919; 6,534,268, and 6,858,431, and in Wozney, J. M., et al. (1988) *Science,* 242(4885):1528-1534.

Growth factors suitable for use in the practice of the invention include but are not limited to bone morphogenic proteins, for example, BMP-2, rhBMP-2, BMP-4, rhBMP-4, BMP-6, rhBMP-6, BMP-7[OP-1], rhBMP-7, GDF-5, and rhGDF-5, as disclosed, for example, in the U.S. Pat. Nos. 4,877,864; 5,013,649; 5,661,007; 5,688,678; 6,177,406; 6,432,919; 6,534,268, and 6,858,431, and in Wozney, J. M., et al. (1988) *Science,* 242(4885):1528-1534.

Suitable antibiotics include, without limitation nitroimidazole antibiotics, tetracyclines, penicillins, cephalosporins, carbopenems, aminoglycosides, macrolide antibiotics, lincosamide antibiotics, 4-quinolones, rifamycins and nitrofurantoin. Suitable specific compounds include, without limitation, ampicillin, amoxicillin, benzylpenicillin, phenoxymethylpenicillin, bacampicillin, pivampicillin, carbenicillin, cloxacillin, cyclacillin, dicloxacillin, methicillin, oxacillin, piperacillin, ticarcillin, flucloxacillin, cefuroxime, cefetamet, cefetrame, cefixine, cefoxitin, ceftazidime, ceftizoxime, latamoxef, cefoperazone, ceftriaxone, cefsulodin, cefotaxime, cephalexin, cefaclor, cefadroxil, cefalothin, cefazolin, cefpodoxime, ceftibuten, aztreonam, tigemonam, erythromycin, dirithromycin, roxithromycin, azithromycin, clarithromycin, clindamycin, paldimycin, lincomycirl, vancomycin, spectinomycin, tobramycin, paromomycin, metronidazole, tinidazole, ornidazole, amifloxacin, cinoxacin, ciprofloxacin, difloxacin, enoxacin, fleroxacin, norfloxacin, ofloxacin, temafloxacin, doxycycline, minocycline, tetracycline, chlortetracycline, oxytetracycline, methacycline, rolitetracyclin, nitrofurantoin, nalidixic acid, gentamicin, rifampicin, amikacin, netilmicin, imipenem, cilastatin, chloramphenicol, furazolidone, nifuroxazide, sulfadiazin, sulfametoxazol, bismuth subsalicylate, colloidal bismuth subcitrate, gramicidin, mecillinam, cloxiquine, chlorhexidine, dichlorobenzylalcohol, methyl-2-pentylphenol or any combination thereof.

Suitable anti-inflammatory compounds include the compounds of both steroidal and non-steroidal structures. Suitable non-limiting examples of steroidal anti-inflammatory compounds are corticosteroids such as hydrocortisone, cortisol, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluocinolone, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone. Mixtures of the above steroidal anti-inflammatory compounds can also be used.

Non-limiting example of non-steroidal anti-inflammatory compounds include nabumetone, celecoxib, etodolac, nimesulide, apasone, gold, oxicams, such as piroxicam, isoxicam, meloxicam, tenoxicam, sudoxicam, and CP-14,304; the salicylates, such as aspirin, disalcid, benorylate, trilisate, safapryn, solprin, diflunisal, and fendosal; the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; the fenamates, such as mefenamic, meclofenamic, flufenamic, niflumic, and tolfenamic acids; the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and the pyrazoles, such as phenylbutazone, oxyphenbutazone, feprazone, azapropazone, and trimethazone.

The various compounds encompassed by this group are well-known to those skilled in the art. For detailed disclosure of the chemical structure, synthesis, side effects, etc. of non-steroidal anti-inflammatory compounds, reference may be had to standard texts, including Anti-inflammatory and Anti-Rheumatic Drugs, K. D. Rainsford, Vol. I-III, CRC Press, Boca Raton, (1985), and Anti-inflammatory Agents, Chemistry and Pharmacology 1, R. A. Scherrer, et al., Academic Press, New York (1974), each incorporated herein by reference.

Mixtures of these non-steroidal anti-inflammatory compounds may also be employed, as well as the pharmologically acceptable salts and esters of these compounds.

In addition, so-called "natural" anti-inflammatory compounds are useful in methods of the disclosed invention. Such compounds may suitably be obtained as an extract by suitable physical and/or chemical isolation from natural sources (e.g., plants, fungi, by-products of microorganisms). Suitable non-limiting examples of such compounds include candelilla wax, alpha bisabolol, aloe vera, Manjistha (extracted from plants in the genus Rubia, particularly Rubia Cordifolia), and Guggal (extracted from plants in the genus Commiphora, particularly Commiphora Mukul), kola extract, chamomile, sea whip extract, compounds of the Licorice (the plant genus/species Glycyrrhiza glabra) family, including glycyrrhetic acid, glycyrrhizic acid, and derivatives thereof (e.g., salts and esters). Suitable salts of the foregoing compounds include metal and ammonium salts. Suitable esters include $C_2$-$C_{24}$ saturated or unsaturated esters of the acids, preferably $C_{10}$-$C_{24}$, more preferably $C_{16}$-$C_{24}$. Specific examples of the foregoing include oil soluble licorice extract, the glycyrrhizic and glycyrrhetic acids themselves, monoammonium glycyrrhizinate, monopotassium glycyrrhizinate, dipotassium glycyrrhizinate, 1-beta-glycyrrhetic acid, stearyl glycyrrhetinate, and 3-stearyloxy-glycyrrhetinic acid, and disodium 3-succinyloxy-beta-glycyrrhetinate.

Generally, anti-inflammatory non-steroid drugs are included in the definition of pain-reducing agents because they provide pain relief. In addition, suitable pain-reducing agents include other types of compounds, such as, for example, opioids (such as, for example, morphine and naloxone), local anaesthetics (such as, for example, lidocaine), glutamate receptor antagonists, α-adrenoreceptor agonists, adenosine, canabinoids, cholinergic and GABA receptors agonists, and different neuropeptides. A detailed discussion of different analgesics is provided in Sawynok et al., (2003) *Pharmacological Reviews,* 55:1-20, the content of which is incorporated herein by reference.

Suitable cells include, without limitations, stem cells, e.g., embryonic or adult stem cells, which can conveniently be derived from blood or bone marrow of the patient or from an allogeneic source, which preferably is immunologically compatible with the patient. Other suitable cells may include chondrogenic or osteogenic precursor cells.

A person of the ordinary skill in the art will also appreciate that different cocktails of the bioactive agents may be included within the upper cap and the at least one insert. Thus, for example, the upper cap may include a chondrogenic agent, a pain-reducing agent and an antibiotic, while the at least one insert may include an osteogenic agent, and an anti-inflammatory agent.

Since both the upper cap and the at least one insert are preferably hydrophilic, the bioactive agent or agents may be incorporated within the upper cap and the at least one insert by simply soaking these structures in solutions of the desired bioactive agents. In another embodiment, the upper cap or the at least one insert or both comprise reservoirs 60 wherein the bioactive agent or agents 62 and 64 are stored (FIG. 8). Such embodiment would be especially advantageous if the bioactive agents are in sustained-release formulations.

Suitable sustained-release formulations include but not limited to capsules, microspheres, particles, gels, coating, matrices, wafers, pills or other pharmaceutical delivery compositions. The examples of such sustained-release formulations have been described previously, for example, in U.S. Pat. Nos. 6,953,593, 6,946,146, 6,656,508, 6,541,033, 6,451,346, the contents of which are incorporated herein by reference. Many methods of preparation of a sustained-release formulation are known in the art and are disclosed in *Remington's Pharmaceutical Sciences* (18th ed.; Mack Publishing Company, Eaton, Pa., 1990), incorporated herein by reference. In one embodiment, the at least one bioactive agent is formulated within microcapsules. Suitable microcapsules can include hydroxymethylcellulose or gelatin-microcapsules and polymethyl methacrylate microcapsules prepared by coacervation techniques or by interfacial polymerization. In addition, microemulsions or colloidal drug delivery systems such as liposomes and albumin microspheres, may also be used. See *Remington's Pharmaceutical Sciences* ($18^{th}$ ed.; Mack Publishing Company Co., Eaton, Pa., 1990).

In another aspect, the invention provides a kit comprising an upper cap; and at least one insert comprising at least one non-polymeric material; wherein a porosity of the upper cap is greater than a porosity of the at least one insert, and a Young's modulus of the upper cap is smaller than a Young's modulus of the at least one insert.

As described above, in the preferred embodiment, the upper cap is made of a polymeric material and at least one insert is made of a ceramic, such as approximately 15% HA and approximately 85% TCP. Thus, in this embodiment, the practitioner would assemble the osteochondral implantable device prior to placing the device into the tissue defect. The kit may be preferable to the pre-assembled device because it allows the practitioner a greater control: for example, upper caps of different sizes may be combined with at least one insert if the collar portions of these upper caps can be matched with the at least one insert.

In another embodiment, the kit further comprises at least one bioactive agent. It may be more economically advantageous to ship the bioactive agent in a lyophilized form, thus prolonging shelf-life and decreasing the shipping cost of the kit. If different cocktails of the bioactive agents are used for the upper cap and the at least one insert, soaking these structures in the solutions containing pre-selected bioactive agents prior to assembly will result in a quicker and more uniform distribution of the bioactive agents within those structures.

The kit may further comprise a bioadhesive, as disclosed above, to secure the upper cap and the at least one insert, or a set of instructions. The instructions would preferably provide information about a safe and effective use of the kit. A person of the ordinary skill in the art will appreciate that the instructions may be provided in a printed, electronic, video- or audio-medium or any combination thereof.

Every patent and non-patent publication cited in the instant disclosure is incorporated into the disclosure by reference to the same effect as if every publication is individually incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

The invention claimed is:

1. An osteochondral implantable device comprising:
    an upper cap comprising a synthetic biodegradable polymer; and
    at least one insert in contact with the upper cap, said at least one insert comprising at least one non-polymeric material comprising a ceramic comprising between about 12% and about 50% hydroxyapatite and between about 50% and about 88% tri-calcium phosphate.

2. The osteochondral implantable device of claim 1, wherein the synthetic biodegradable polymer comprises polylactic acid, polyglycolic acid, polylacticpolyglycolic acid, polyorthoesters, Polycapralactone, Polydiaxonone, Polyvynal Fumarate, or any combination thereof.

3. The osteochondral implantable device of claim 1, wherein the upper cap comprises a co-polymer of lactic and glycolic acids.

4. The osteochondral implantable device of claim 1, wherein the at least one insert further comprises bone.

5. The osteochondral implantable device of claim 4, wherein the bone is an allograft bone.

6. The osteochondral implantable device of claim 1, wherein the ceramic comprises calcium phosphate dibasic, calcium sulfate, calcium carbonate, or any combination thereof.

7. The osteochondral implantable device of claim 1, wherein the ceramic comprises about 30% hydroxyapatite and about 70% tri-calcium phosphate.

8. The osteochondral implantable device of claim 1, wherein the ceramic comprises about 15% hydroxyapatite and about 85% tri-calcium phosphate.

9. The osteochondral implantable device of claim 1, wherein the upper cap comprises at least one collar portion to receive at least a portion of the at least one insert.

10. The osteochondral implantable device of claim 9, wherein the at least one collar portion comprises at least one window.

11. The osteochondral implantable device of claim 10, wherein the at least one insert comprises at least one protrusion such that the at least one protrusion of the at least one insert fits into the at least one window of the at least one collar portion when the osteochondral implantable device is assembled.

12. The osteochondral implantable device of claim 9, wherein the at least one collar portion of the upper cap is shaped to secure the at least one insert.

13. The osteochondral implantable device of claim 12, wherein the at least one collar portion of the upper cap is shaped to secure the at least one insert by a bayonet-type lock.

14. The osteochondral implantable device of claim 1 further comprising at least one bioactive agent.

15. The osteochondral implantable device of claim 14 wherein the at least one bioactive agent is selected from the group consisting of osteogenic agents, chondrogenic agents, antibiotics, anti-inflammatory agents, pain-reducing agents, anti-catabolic agent, anabolic agent, analgesic agent and any combination thereof.

16. The osteochondral implantable device of claim 14 wherein the at least one bioactive agent is included within the at least one upper cap.

17. The osteochondral implantable device of claim 14 wherein the at least one bioactive agent is included within the at least one insert.

18. The osteochondral implantable device of claim 14 wherein the at least one bioactive agent is BMP-2.

19. The osteochondral implantable device of claim 1, wherein the upper cap has a predetermined shape.

20. The osteochondral implantable device of claim 1 further comprising a non-porous film covering at least a portion of the upper cap, wherein said at least the portion is exposed to synovial fluid when the osteochondral implantable device is placed into a tissue defect.

21. The osteochondral implantable device of claim 1, wherein at least one of the upper cap and the at least one insert comprises at least one reservoir.

22. The osteochondral implantable device of claim 21, wherein the at least one reservoir contains at least one bioactive agent.

23. The osteochondral implantable device of claim 22, wherein the at least one bioactive agent is in a sustained-release form.

24. The osteochondral implantable device of claim 1, with the proviso that the osteochondral implantable device does not include a fixation device which is embedded within the osteochondral implantable device and insertable into a tissue receptacle.

25. The osteochondral implantable device of claim 1, wherein a porosity of the upper cap is greater than a porosity of the at least one insert, and a Young's modulus of the upper cap is smaller than a Young's modulus of the at least one insert.

26. The osteochondral implantable device of claim 1, wherein the upper cap comprises a surfactant comprising metal soaps of fatty acids, alkyl aryl sulfonic acids, linear aklylbenzene sulfonates, alky sulfates, alcohol ethoxylates, alcohol ethoxy sulfates, alkylphenol ethoxylates, alpha olefin sulfonates, secondary alkane sulfonates, or alpha olefin sulfonates.

27. A kit comprising:
an upper cap comprising a synthetic biodegradable polymer; and
at least one insert comprising at least one non-polymeric material comprising a ceramic comprising between about 12% and about 50% hydroxyapatite and between about 50% and about 88% tri-calcium phosphate.

28. The kit of claim 27 further comprising a set of instructions.

29. The kit of claim 27 further comprising at least one bioactive agent.

30. The kit of claim 29, wherein the at least one bioactive agent is BMP.

31. The kit of claim 27, further comprising a bioadhesive capable of securing the upper cap and the at least one insert in a fixed attachment.

32. The kit of claim 27, wherein a porosity of the upper cap is greater than a porosity of the at least one insert, and a Young's modulus of the upper cap is smaller than a Young's modulus of the at least one insert.

33. The osteochondral implantable device of claim 1, wherein the upper cap comprises a non-toxic anionic surfactant, a cationic surfactant, an amphoretic surfactant, or a nonionic surfactant.

34. The osteochondral implantable device of claim 33, wherein the non-toxic anionic surfactant, the cationic surfactant, the amphoretic surfactant, and the nonionic surfactant are compatible with the upper cap and/or the at least one insert.

* * * * *